United States Patent [19]
Kameyama et al.

[11] Patent Number: 4,822,872

[45] Date of Patent: Apr. 18, 1989

[54] METHOD OF PURIFYING FACTOR VIII

[75] Inventors: Syojyu Kameyama, Kyoto; Hideo Nishimaki, Nara; Yoshiro Iga, Osaka; Tadakazu Suyama, Kyoto, all of Japan

[73] Assignee: Green Cross Corporation, Osaka, Japan

[21] Appl. No.: 50,105

[22] Filed: May 15, 1987

[30] Foreign Application Priority Data

May 15, 1986 [JP] Japan .................. 61-109376

[51] Int. Cl.$^4$ .................. A61K 35/14; A23J 1/00
[52] U.S. Cl. .................. 530/383; 530/413; 525/54.1; 210/656; 210/661; 210/679
[58] Field of Search .............. 530/383, 412, 413, 812, 530/813, 814, 815, 816; 525/54.1; 210/656, 660, 661, 679

[56] References Cited

U.S. PATENT DOCUMENTS 4,381,239  4/1983  Chibata et al. .................. 210/679

Primary Examiner—John Kight
Assistant Examiner—Nathan M. Nutter
Attorney, Agent, or Firm—Sughrue, Mion, Zinn, Macpeak, and Seas

[57] ABSTRACT

A method for purifying factor VIII complex comprising: (A) absorbing an impure extract containing factor VIII complex on a water-insoluble carrier, and (B) recovering factor VIII complex in the unadsorbed fractions, wherein said water-insoluble carrier contains as a ligand a group represented by the formula (I) or (II):

$$-(CH_2)_n-NH_2 \quad \text{(I) or}$$

$$-(CH_2)_n-CHO \quad \text{(II)}$$

wherein n is an integer of from 3 to 10.

5 Claims, 1 Drawing Sheet

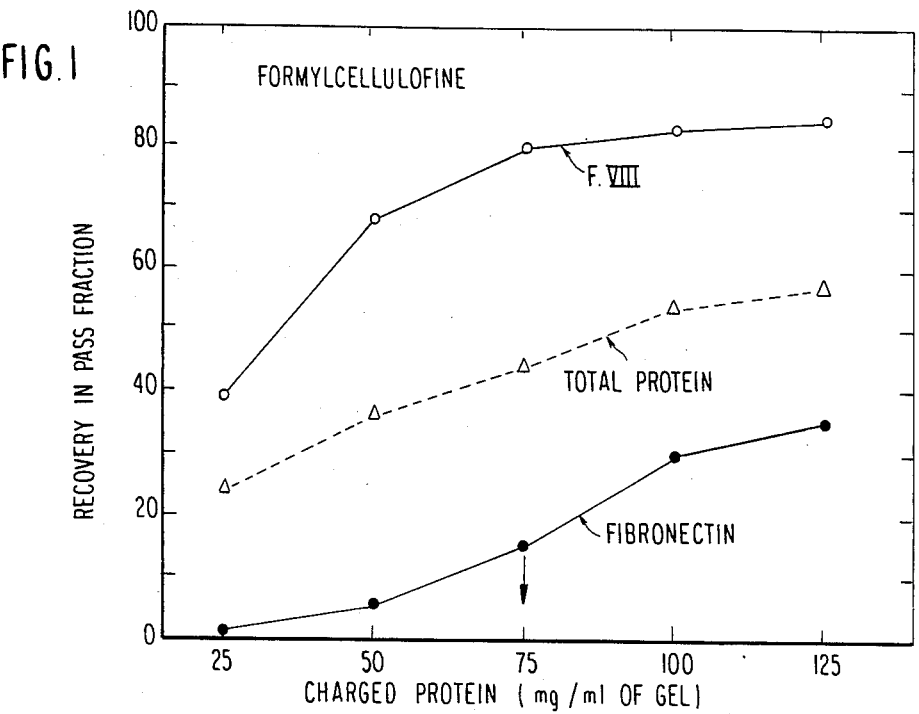
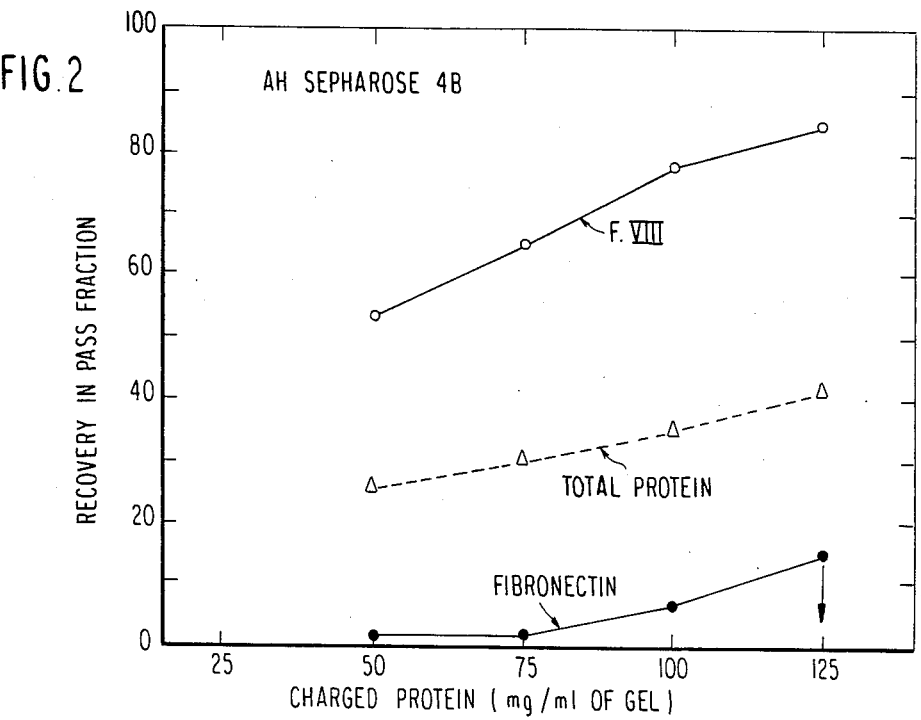

METHOD OF PURIFYING FACTOR VIII

FIELD OF THE INVENTION

The present invention relates to a method of purifying an antihemophilic factor (AHF) that comprises the coagulation factor for factor VIII and factor VIII related von Willebrand's protein.

BACKGROUND OF THE INVENTION

Coagulation factor VIII is a complex of blood proteins that is involved in the initial stage of blood coagulation. Factor VIII exists in a very small amount in normal plasma circulation as a high-molecular weight glycoprotein. This complex is made of a coagulation promoting component (factor VIIIC) that does not exist in patients with hemophilia A, and factor VIII related von Willebrand's protein (factor VIIIR: vWp) that is associated with platelet aggregation and adhesiveness. The latter proteinaceous component undergoes quantitative or qualitative changes in the plasma of patients with von Willebrand's disease. The complex of these two components is believed to be bound to lipoproteins which impart additional stability to the complex in vivo. It is also believed that calcium ions present in optimal concentrations impart additional stability to factor VIIIC.

Hemorrhagic diseases such as hemophilia A and von Willebrand's disease can most effectively be treated by supplementation of factor VIIIC or von Willebrand's factor. This is accomplished by intravenous injection of fresh plasma or a "cryoprecipitate" (a cold plasma precipitate) if the disease is moderate and by administration of an AHF concentrate if the disease is serious.

A cold plasma precipitate is usually prepared by the method described in Pool et al. *Nature* 203:312 (1964). According to this method, plasma is frozen and slowly thawed at 4° C. to obtain a cold plasma precipitate or cryoprecipitate that is readily re-dissolvable at 37° C. The majority of factor VIII present in the plasma can be recovered in this cryoprecipitate which therefore is a convenient source of supply of a concentrated form of factor VIII that can be used for therapeutic purposes.

Attempts at treating hemophilia A or von Willebrand's disease with fresh whole blood or plasma or a cryoprecipitate have serious disadvantages. For instance, the low concentrations of AHF necessitate administering fairly large quantities of solution to patients by intravenous injection. Therefore, transfusion must be carried out by instillation or intravenous drip. Another problem is that the fibrinogens present in large amounts will sometimes cause undesired side-effects during transfusion (see Yoshioka et al., Rinshio Ketsueki (*Clinical Blood*), 17: 788 (1976)). The use of an AHF concentrate has the advantage that a comparatively small amount (about 10–40 ml) of solution is sufficient to provide the patient with the required amount of factor VIII. However, a problem still exists in that factor VIII, which is present in plasma in a very small amount, is highly labile and inevitably suffers activity loss during the separation and purification procedures. Since the AHF concentrate requires a fairly large number of steps for its preparation, the recovery of factor VIII from the starting plasma is too low to realize efficient utilization of the precious starting material. The percentage recovery from the starting plasma is generally about from 40 to 60% for the cryoprecipitate and from 10 to 40% for the AHF concentrate (see Baugh et al., *Biochemica Biophysica Acta*, 371:360 (1974), and Olsen et al., J. Lab. Clin. Med., 89:1278 (1977)).

SUMMARY OF THE INVENTION

The present invention has solved the above-described problems and provides a method for purifying factor VIII complex (A) by adsorbing an impure extract containing factor VIII complex on a water-insoluble carrier and (B) recovering factor VIII complex thereof in the unadsorbed fractions, wherein the water-insoluble carrier contains, as a ligand, a group represented by formula (I) or (II):

$$-(CH_2)_n-NH_2 \qquad (I)$$

$$-(CH_2)_n-CHO \qquad (II)$$

where n is an integer of from 3 to 10.

BRIEF DESCRIPTION OF THE DRAWINGS

FIG. 1 is a graph representing the relationship between the amount of charged protein and the recovery of each component contained in the non-adsorbed fraction (factor VIII, fibronectin, total protein content) when Formylcellulofine is used.

FIG. 2 is a graph representing the relationship between the amount of charged protein and the recovery of each of component contained in the non-adsorbed fraction (factor VIII, fibronectin, total protein content) when AH-Sepharose is used.

DETAILED DESCRIPTION OF THE INVENTION

(a) Starting material

In the method of the present invention, any fraction that is derived from blood can be used as starting material as far as it contains factor VIII. Specific examples of factor VIII-containing fraction include cryoprecipitate, a Cohn's fraction I which is prepared from blood by cold ethanol fractionation. The cryoprecipitate is a precipitate obtained by freezing and thawing plasma. The starting material is suspended in a buffer solution of low molar concentration (e.g., 0.001 to 0.05 M) and adjusted to have a pH between about 6.4 to 7.5 (By this operation inactivation of by nature extremely labile factor VIII can be prevented). Thus, factor VIII is extracted. The buffer solution in which the thawed cryoprecipitate is to be suspended (e.g., pH 6.4 to 7.5) contains a variety of physiological buffering agents at low molar concentrations (e.g., 0.001 to 0.05 M), such as imidazole, sodium phosphate, ammonium bicarbonate, EACA, glycine, and Tris (i.e., tris(hydroxymethyl)aminomethane). Many other physiological buffering agents that achieve the stabilizing effect can also be employed. Additional components of the buffer solution include low molar concentrations (e.g., 0.001 to 0.05 M) of physiological salts such as sodium chloride for preventing agglutination of proteins and low molar concentrations (e.g., 0.001 to 0.05 M) of physiological anticoagulation factors such as sodium citrate, which absorb excess calcium ions and thereby prevent coagulation of fibrinogens. Although not essential, it is sometimes preferable for most of the proteins present in trace amounts in the cryoprecipitate to be removed by a variety of purifying techniques before the cryoprecipitate is subjected to the treatment intended by the present invention. One applicable method to achieve this objective is to permit the undesired protein, such as factors VII, IX and X and prothrombin (factor II) in the blood to be adsorbed on an aluminum hydroxide gel (U.S. Pat. No. 4,170,693). Other methods such as a gel filtration method as described in U.S. Pat. No. 3,637,489 and a method using anion exchange resin as described in Japanese Patent Application (OPI) No. 125609/77 can also be employed.

The extract of the cryoprecipitate may be purified to intermediate degrees by such techniques as fractionation with glycine as described in U.S. Pat. No. 3,652,530 or with PEG (polyethylene glycol) as described in U.S. Pat. No. 3,631,018 and the resulting impure solution containing factor VIII complex can also be advantageously used as a starting material.

(b) Water-insoluble carrier

The water-insoluble carrier used in the present invention contains, as a ligand, a group represented by formula (I), $-(CH_2)_n-NH_2$, or (II), $-(CH_2)_n-CHO$, where n is an integer of from 3 to 10, preferably 4 to 8. Preferable examples of the group include $-CH_4H_8NH_2$ (aminobutyl group), $-C_6H_{12}NH_2$ (aminohexyl group), $-C_8H_{16}NH_2$ (aminooctyl group), $-C_{10}H_{20}NH_2$ (aminodecyl group), and $-(CH_2)_4-CHO$ (formylbutyl group). Any water-insoluble carrier may be employed so long as it allows for incorporation of these groups, Specific examples of advantageous water-insoluble carriers include water-insoluble polysaccharides such as agarose, cellulose, Sephacryl (product of Pharmacia Fine Chemicals) and Sephadex (product of Pharmacia Fine Chemicals), and polyvinyl-based gels such as gels of polystyrene, polyacrylamide, polyvinyl acetate, etc.

Commercial products of water-insoluble carriers containing these groups are currently available and they include ω-am inoalkylagarose series (products of Miles Laboratories, Inc.) and Formylcellulofine [cellulose-O-CH$_2$—CHOH—CH$_2$—NH—(CH$_2$)$_4$—CHO] (produced by Seikagaku Kogyo Co., Ltd.). Other versions can be readily produced by employing the methods used to manufacture these commercial products or by slight modifications of such methods.

The purifying step of the method of the present invention is typically accomplished by bringing the starting material (i.e., an aqueous solution containing factor VIII complex) into contact with the water-insoluble carrier containing the group represented by the formula (I) or (II). This may be achieved by any known adsorption technique such as a method wherein the starting material is passed through a column packed with the water-insoluble carrier or by a batch system. Adsorption is performed generally at a temperature of 10° to 30° C., preferably 15° to 25° C. or room temperature for a period of 10 minutes to 3 hours, preferably 30 minutes to 2 hours. Before being contacted with the starting material, the water-insoluble carrier is equilibrated with a buffer solution of low salt concentration (e.g., 0.01 M sodium citrate) having a pH of about 6–8.

(c) Recovery of Factor VIII

Factor VIII complex is recovered in the unadsorbed fractions. Selective elution of the adsorbed proteins can be accomplished by washing the water-insoluble carrier with aqueous solutions that have the same or different pHs and which contain progressively increasing concentrations of salts. The change of salt concentrations may be continuous (e.g., linear) or discontinous.

The method of the present invention is capable of at least 80% recovery of factor VIII complex and a 2- to 10-times increase of its specific activity. Any of the contaminant proteins (i.e., fibronectin and fibrinogen) contained in the cryoprecipitate are adsorbed on the carrier and thereby removed from the cryoprecipitate.

By employing the method of the present invention, factor VIII complex of high purity can be recovered conveniently and in a high yield from an impure extract containing factor VIII complex as in a cryoprecipitate. Therefore, the method can be used with much advantage in preparing factor VIII complex on an industrial scale.

The following examples are provided for the purpose of further illustrating the present invention but are in no way to be taken as limiting.

EXAMPLE 1

Twenty grams of a cryoprecipitate obtained from blood was subjected to extraction with five volumes (100 ml) of buffer solution A (pH 6.9) comprising 0.02 M Tris and 0.01 M citric acid. The resulting extract was brought into contact with an aluminum hydroxide gel in an amount that was one tenth the volume of the cryoprecipitate (0.25 mg/ml). The mixture was centrifuged (5,000×g, 15 minutes) at room temperature and the supernatant was recovered. To the recovered supernatant, AH-Sepharose (aminohexyl Sepharose) that had been equilibrated with buffer solution A was added in an amount of 4, 2, 1, 0.5 or 0.25 g per 10 ml of the supernatant and the two components were mixed under stirring for 60 minutes at room temperature. The mixture was then passed through a glass filter and the filtrate was recovered. The content of factor VIIIC in the filtrate was measured by the so-called "one-step method" (see Hardisty et al., Thromb. Diath. Haemorrh., 7:219–229 (1962). The contents of the other physiologically active substances in the filtrate, i.e. fibrinogen and fibronectin, were determined with a Fibrinogen Assay Kit (Dado Corporation) and a fibronectin Assay Kit (Boehringer, Mann.), respectively. The total protein content was measured by the method described in Gornall et al. J. Biol. Chem., 177:751 (1949).

The results are shown in Table 1 which demonstrates the ability of the method of the present invention to achieve selective recovery of factor VIIIC.

TABLE 1

| AH—Sepharose (g/ml) | Factor VIIIC U(%) | Fibrinogen mg(%) | Fibronectin mg(%) | Total Protein mg(%) |
| --- | --- | --- | --- | --- |
| Not Added | 64.8(100) | 148.2(100) | 40.4(100) | 237.5(100) |
| 0.4 | 56.9(87.8) | 22.1(14.9) | 1.9(4.6) | 46.3(19.5) |
| 0.2 | 60.2(92.9) | 64.8(43.7) | 8.2(20.3) | 104.3(43.9) |
| 0.1 | 61.9(95.5) | 98.1(66.2) | 19.4(48.0) | 154.9(65.2) |
| 0.05 | 62.2(96.0) | 109.7(74.0) | 25.8(63.9) | 186.9(78.7) |
| 0.025 | 64.2(99.0) | 129.1(87.1) | 35.0(86.6) | 208.1(87.6) |

EXAMPLE 2

A commercial preparation of factor VIII concentrate (Concoeight-HT of Green Cross Corporation) was dissolved in the accompanying solubilizing fluid. The resulting solution was dialyzed against a buffer solution (0.01 M citric acid; pH 7.0) at room temperature. To 10 ml of the dialyzate was added 10% (w/v) aqueous sodium chloride to prepare solutions having final NaCl concentrations of 0, 0.5, 1.0, 1.5 and 2.0%. To each of these solutions, 1.0 g of AH-Sepharose equilibrated with the same buffer solution as used above was added and mixed under stirring for 60 minutes at room temperature. The resulting mixtures were passed through a glass filter and the recovered filtrates were subjected to analyses. The activity of recovered factor VIIIC was determined by the same method as employed in Example 1. The results are shown in Table 2.

TABLE 2

| AH—Sepharose Treatment (g/ml) | NaCl Concentration (%) | Factor VIIIC U(%) | Total Protein mg(%) | Specific Activity U/mg |
|---|---|---|---|---|
| — | 0(3) | 259(100) | 314(100) | 0.82 |
| + | 0(3) | 210(81.1) | 50(15.9) | 4.20 |
| + | 0.5(16) | 189(73.0) | 57(18.2) | 3.32 |
| + | 1.0(30) | 153(59.1) | 76(24.2) | 2.01 |
| + | 1.5(43) | 106(40.9) | 123(39.2) | 0.86 |
| + | 2.0(56) | 73(28.2) | 176(56.1) | 0.41 |

EXAMPLE 3

Twenty grams of a cryoprecipitate was subjected to extraction with five volumes (100 ml) of buffer solution A. The resulting extract was brought into contact with an aluminum hydroxide gel in an amount of one tenth the volume of the cryoprecipitate (0.25 mg/ml) and the residual prothrombin was removed by adsorption on the gel. The unadsorbed fractions were centrifuged (5,000×g, 15 minutes) and the resulting supernatant was mixed with 0.15 g/ml of glycine so as to remove any residual fibrinogen. After performing additional centrifugation (5,000×g, 15 minutes), the supernatant was recovered and to 10 ml-portions of the recovered supernatant, aminohexyl-Sepharose equilibrated with buffer solution A was added in an amount of 0.25, 0.5, 0.75 or 1.0 g and mixed under stirring for 60 minutes at room temperature. The mixtures were then passed through a glass filter and the filtrates were recovered. Analyses were conducted as in Example 1 and the results are shown in Table 3.

TABLE 3

| AH—Sepharose Treatment (g) | Factor VIIIC U(%) | Fibronectin mg(%) | Total Protein mg(%) |
|---|---|---|---|
| 0 | 48.3(100) | 24.3(100) | 137.0(100) |
| 0.5 | 48.0(99.4) | 9.5(39.1) | 91.8(67.0) |
| 1.0 | 42.5(88.0) | 6.1(25.1) | 74.0(54.0) |
| 1.5 | 40.1(83.0) | 2.4(9.9) | 50.8(37.1) |
| 2.0 | 38.8(80.3) | 1.5(6.2) | 38.4(28.0) |

EXAMPLE 4

The procedures of Example 1 were repeated except that phenyl-Sepharose and octyl-Sepharose were used as two control adsorbents for making comparison with AH-Sepharose. Each of these adsorbents was used in amounts of both 1.0 and 2.0 g/10 ml. The results are shown in Table 4 from which one can see that AH-Sepharose was more effective in achieving selective recovery of factor VIIIC.

TABLE 4

| Adsorbent | Amount (g) | Factor VIIIC U(%) | Fibrinogen mg(%) | Fibronectin mg(%) | Total Protein mg(%) |
|---|---|---|---|---|---|
| — | — | 65.0(100) | 128.0(100) | 28.8(100) | 336.0(100) |
| Phenyl-Sepharose | 1.0 | 63.9(98.3) | 82.9(64.8) | 24.6(85.4) | 237.1(70.6) |
| Phenyl-Sepharose | 2.0 | 63.1(97.1) | 34.2(26.7) | 17.3(60.1) | 136.8(40.7) |
| Octyl-Sepharose | 1.0 | 64.6(99.4) | 118.1(92.3) | 28.5(99.0) | 315.2(93.8) |
| Octyl-Sepharose | 2.0 | 63.7(98.0) | 103.7(81.0) | 25.5(88.5) | 272.5(81.1) |
| AH—Sepharose | 1.0 | 63.7(98.0) | 76.8(60.0) | 10.3(35.8) | 199.2(59.3) |
| AH—Sepharose | 2.0 | 59.0(90.8) | 32.3(25.2) | 0.9(3.1) | 108.9(32.4) |

EXAMPLE 5

The procedures of Example 1 were repeated except that AH-Sepharose and Formylcellulofine were used as adsorbents each in an amount of 0.04, 0.02, 0.013, 0.01 or 0.008 ml (as gel) per mg protein in the supernatant. In other words, the amount of charged protein was 25, 50, 75, 100 or 125 mg/ml of gel.

Recovery in terms of factor VIII C activity was determined in the same manner as in Example 1.

The results obtained are shown in FIG. 1 (Formylcellulofine) and FIG. 2 (AH-Sepharose).

While the invention has been described in detail and with reference to specific embodiment thereof, it will be apparent to one skilled in the art that various changes and modifications can be made therein without departing from the spirit and scope thereof.

What is claimed is:

1. A method for purifying factor VIII complex comprising: (A) adsorbing an impure extract containing factor VIII complex on a water-insoluble carrier, and (B) recovering factor VIII complex in the unadsorbed fractions, wherein said water-insoluble carrier contains as a ligand a group represented by the formula (I) or (II):

wherein n is an integer of from 3 to 10.

2. The method as claimed in claim 1, wherein said water-insoluble carrier contains a ligand represented by the group consisting of an aminobutyl group, an aminohexyl group, an aminooctyl group, an aminodecyl group and a formylbutyl group.

3. The method as claimed in claim 1, wherein said water-insoluble carrier is selected from the group consisting of water-insoluble polysaccharide and polyvinyl-based gel.

4. The method as claimed in claim 3, wherein said polysaccharide is selected from the group consisting of agarose and cellulose.

5. The method as claimed in claim 1, wherein said impure extract is a cryoprecipitate of plasma.

* * * * *